(12) United States Patent
Singer et al.

(10) Patent No.: US 9,554,936 B2
(45) Date of Patent: *Jan. 31, 2017

(54) SINGER-DOMANSKI RESIN MMF/REIMPLANTATION DEVICE

(71) Applicants: Lawrence D. Singer, Arlington, VA (US); Mark C. Domanski, Arlington, VA (US)

(72) Inventors: Lawrence D. Singer, Arlington, VA (US); Mark C. Domanski, Arlington, VA (US)

(73) Assignees: Lawrence D. Singer, Arlington, VA (US); Mark C. Domanski, Arlington, VA (US)

( * ) Notice: Subject to any disclaimer, the term of this patent is extended or adjusted under 35 U.S.C. 154(b) by 485 days.

This patent is subject to a terminal disclaimer.

(21) Appl. No.: 13/837,191

(22) Filed: Mar. 15, 2013

(65) Prior Publication Data

US 2013/0295517 A1 Nov. 7, 2013

Related U.S. Application Data

(63) Continuation-in-part of application No. 13/465,558, filed on May 7, 2012.

(51) Int. Cl.
*A61C 5/14* (2006.01)
*A61F 5/058* (2006.01)
(Continued)

(52) U.S. Cl.
CPC ......... *A61F 5/05891* (2013.01); *A61B 17/663* (2013.01); *A61C 7/36* (2013.01)

(58) Field of Classification Search
CPC . A61C 5/007; A61F 5/05891; A61K 2300/00; A61K 9/0097; A61K 9/5138; A61K 9/5192; A61K 33/38; A61K 33/40; A61K 36/886; A61K 6/083; A61K 6/087; A61K 6/09; A61K 9/14; A61K 9/5153; A61K 45/06; A61K 6/0205
(Continued)

(56) References Cited

U.S. PATENT DOCUMENTS 3,675,327 A * 7/1972 Huget et al. ............... 433/215
4,202,328 A    5/1980 Sukkarie
(Continued)

OTHER PUBLICATIONS

David S. Utley et al. "Direct Bonded Orthodontic Brackets for Maxillomandibular Fixation", The Laryngoscope 108: Sep. 1998, pp. 1338-1345.
(Continued)

*Primary Examiner* — Michael Brown
(74) *Attorney, Agent, or Firm* — Global IP Counselors, LLP

(57) ABSTRACT

A resin MMF/reimplantation kit is provided with a dental arch bar that includes an elongated pliable splint and a plurality of attachment members. The pliable splint includes an interiorly facing side surface and an exteriorly facing side surface. The pliable splint includes a curable component that cures from a moldable state to a rigid state in less than one minute upon being activated. The attachment members can be ether partially embedded in the pliable splint or can be separate from the pliable splint until after the pliable splint is attached to the patient's teeth.

20 Claims, 7 Drawing Sheets

(51) Int. Cl.
*A61C 7/36* (2006.01)
*A61B 17/66* (2006.01)

(58) Field of Classification Search
USPC .......................................... 128/848, 859–862
See application file for complete search history.

(56) References Cited

U.S. PATENT DOCUMENTS

| | | | |
|---|---|---|---|
| 4,433,960 A | | 2/1984 | Garito et al. |
| 4,505,672 A | | 3/1985 | Kurz |
| 4,639,219 A | | 1/1987 | Gagin |
| 4,894,012 A | * | 1/1990 | Goldberg et al. ............. 433/215 |
| 4,904,188 A | | 2/1990 | Baurmash |
| 5,087,202 A | | 2/1992 | Krenkel |
| 5,173,048 A | | 12/1992 | Summer |
| 5,184,955 A | | 2/1993 | Baer et al. |
| 5,323,787 A | * | 6/1994 | Pratt ............................. 128/862 |
| 5,785,525 A | | 7/1998 | Weissman |
| 6,086,365 A | * | 7/2000 | Fields ............................ 433/18 |
| 6,120,288 A | | 9/2000 | Deslauriers |
| 6,257,884 B1 | | 7/2001 | Chang |
| 6,983,752 B2 | | 1/2006 | Garabadian |
| 7,048,542 B2 | | 5/2006 | Von Arx et al. |
| 7,351,058 B2 | | 4/2008 | Fore et al. |
| 2003/0044754 A1 | | 3/2003 | Deslauriers et al. |
| 2005/0282115 A1 | | 12/2005 | Gedebou |
| 2007/0283967 A1 | | 12/2007 | Bailey |
| 2009/0170050 A1 | | 7/2009 | Marcus |
| 2010/0095970 A1 | | 4/2010 | Katz et al. |
| 2010/0124727 A1 | | 5/2010 | Shah et al. |
| 2010/0209866 A1 | | 8/2010 | Pitnick et al. |
| 2011/0152951 A1 | | 6/2011 | Baker |
| 2011/0287376 A1 | | 11/2011 | Walther |

OTHER PUBLICATIONS

Vivek Shetty et al. "Do the Benefits of Rigid Internal Fixation of Mandible Fratactures Justify the Added Costs? Results From a Randomized Controlled Trial", Basic and Patient-Oriented Research, pp. 2203-2212.
Letters to Editor, Bonding As an Overdue Replacement of the Wiring of Arch Bars, J Oral Maxillofac Surg, 64:1701-1705, 2006.
Letters to Editor, Comparing The Titanium Arch Bar With the Bonded Arch Bar, doi:10.1016/Journel of JOMS, p. 359-362, Nov. 2006.
International Search Report of corresponding International Application No. PCT/US13/39752, dated on Aug. 16, 2013.

* cited by examiner

SINGER-DOMANSKI RESIN MMF/REIMPLANTATION DEVICE

CROSS-REFERENCE TO RELATED APPLICATIONS

This application is a continuation-in-part application of U.S. patent application Ser. No. 13/465,558 filed on May 7, 2012. The entire disclosure of U.S. patent application Ser. No. 13/465,558 is hereby incorporated herein by reference.

BACKGROUND

Field of the Invention

The present invention generally relates to reconstructive oral surgery due to facial trauma. More specifically, the present invention relates to a resin MMF/reimplantation device (e.g., an intermaxillary fixation device) that used in restoration and healing of maxillo-mandibular injuries such as temporary fixation of teeth and/or jaw segments.

Background Information

Sometimes a person fractures his or her jaw or mandible. Jaw fractures often occur because of interpersonal trauma or fights, motor vehicle accidents and sporting injuries or falls. Typically, jaw fractures require treatment, and surgery is often recommended. There are two main systems that are in use today for immobilizing a person's jaw. The first main system uses metal arch bars (e.g., Erich arch bars that are made of fully annealed stainless steel) which are typically to temporarily attach to the patient's teeth by circumdental wires, while the second main system uses maxillomandibular fixation (MMF) screws.

In order to reduce and stabilize jaw fractures (intermaxillary fixation) with arch bars, the patient's teeth are wired together using arch bars to immobilize the jaw. In particular, two or more arch bars are attached to the patient's teeth by circumdental wires. The arch bars are cut to the appropriate lengths and are secured by the circumdental wires which are looped tightly around the teeth. The upper and lower jaws are drawn together by tightening inter-arch wires that are looped around hooks carried on each arch bar.

In order to stabilize jaw fractures (intermaxillary fixation) with MMF screws, the patient's teeth are wired together using MMF screws that are screwed into patient to immobilize the jaw. The upper and lower jaws are drawn together by tightening wires that are pulled through holes in MMF screws and then tightened.

This conventional wiring procedures using arch bars or MMF screws requires high levels of advanced medical and dental training. Moreover, these two procedures are potentially very traumatic to the patient. Both arch bars and MMF screws are very irritating to patient's natural intraoral soft tissue and can cause damage and infection. During placement of conventional arch bars, the patient's gums are typically penetrated or pierced in an iatrogenic manner during wiring with circumdental wires. During placement of MMF screws, bore holes are created in the jaw using an osteotome that can result in tooth root damage. As circumdental wires are sharp and easily penetrate surgical gloves, their use places the surgeon at risk of blood born pathogens such as HIV and hepatitis. Additionally, conventional procedures that utilize circumdental wires or MMF screws are also very time consuming for both the wiring procedure and the removal procedure. Also removal of the arch bars can be very painful for the patient.

In view of the problems in these conventional wiring procedures, alternative procedures have been developed in which the arch bars are directly bonded to the patient's teeth without using circumdental wiring. However, these directly bonded arch bars do not provide for a simplified and efficient manner in which the arch bars may be secured or stabilized to the teeth prior to the adhesive drying. This may prevent the arch bars from staying stationary during the adhesive process. Additionally, many of these arch bars are manufactured using a metal mesh, in which the application of the metal mesh proves to be difficult to achieve high bonding strength to the patient's teeth.

One example, an arch bar that is directly bonded to the patient's teeth without using circumdental wiring is disclosed in U.S. Pat. No. 4,904,188. This patent discloses an arch bar that includes a plurality of ligature hooks and a metallic mesh layer on the back surface of the arch bar. The metallic mesh layer forms an adhesive bonding attachment structure for attaching the arch bar to the tooth enamel. Other examples of arch bars that are directly bonded to the patient's teeth without using circumdental wiring are disclosed in U.S. Pat. No. 5,087,202 and U.S. Pat. No. 5,184,955.

SUMMARY

Both MMF screws and conventional arch bars have a tendency to loosen over time as the wires deform under the force of the patient's muscles of mastication. This may necessitate reoperation in some cases or a poorer healing result. The dental arch bar of the present disclosure is not subject to deformation. Another advantage of the dental arch bar of the present disclosure is that is they can be used to stabilize/reimplant teeth, where MMF screws cannot, while conventional Erich arch bars typically do a poor job and/or are not suitable in most cases. Thus, the dental arch bar of the present disclosure is more flexible and has greater range of application as compared to the conventional arch bars and the MMF screws.

In view of the state of the known technology, there exists a need for a less invasive and less time consuming procedure for immobilizing a person's jaw. Thus, a dental arch bar is presented in this disclosure that is directly bond to a patient's teeth so as to avoid the trauma of the conventional wiring procedure. Also the dental arch bar of this disclosure is relatively easy to use and decreases the surgery time in comparison to the conventional procedures that are discussed above. Further, the dental arch bar of this disclosure is safer for surgeons to apply much more quickly than conventional systems.

In view of the state of the known technology, one aspect presented in this disclosure is to provide a dental arch bar that basically comprises an elongated pliable splint and a plurality of individual spaced apart attachment members. The pliable splint includes an interiorly facing side surface and an exteriorly facing side surface. The pliable splint includes a curable component that cures from a moldable state to a rigid state being activated. Each of the attachment members is partially embedded in the pliable splint with each of the attachment members having a protuberance portion extending outwardly from the exteriorly facing side surface of the pliable splint.

In another aspect presented in this disclosure is to provide a resin MMF/reimplantation kit that at least comprises an elongated pliable splint and a plurality of individual attachment members. The pliable splint includes an interiorly facing side surface and an exteriorly facing side surface. The pliable splint includes a curable component that cures from a moldable state to a rigid state upon being activated. The attachment members includes an anchoring portion configured to be at least partially embedded in the pliable splint, and a protuberance portion extending from the anchoring portion. The protuberance portion is configured to be disposed on the exteriorly facing side surface of the pliable splint upon at least partially embedding the anchoring portion in the elongated pliable splint.

This aspect and other aspects, objects, features and advantages of the disclosed dental arch bar will become apparent to those skilled in the art from the following detailed description, which, taken in conjunction with the annexed drawings, discloses preferred embodiments.

BRIEF DESCRIPTION OF THE DRAWINGS

Referring now to the attached drawings which form a part of this original disclosure.

DETAILED DESCRIPTION OF EMBODIMENTS

Selected embodiments will now be explained with reference to the drawings. It will be apparent to those skilled in the dental field from this disclosure that the following descriptions of the embodiments are provided for illustration only and not for the purpose of limiting the invention as defined by the appended claims and their equivalents.

Figure 1:
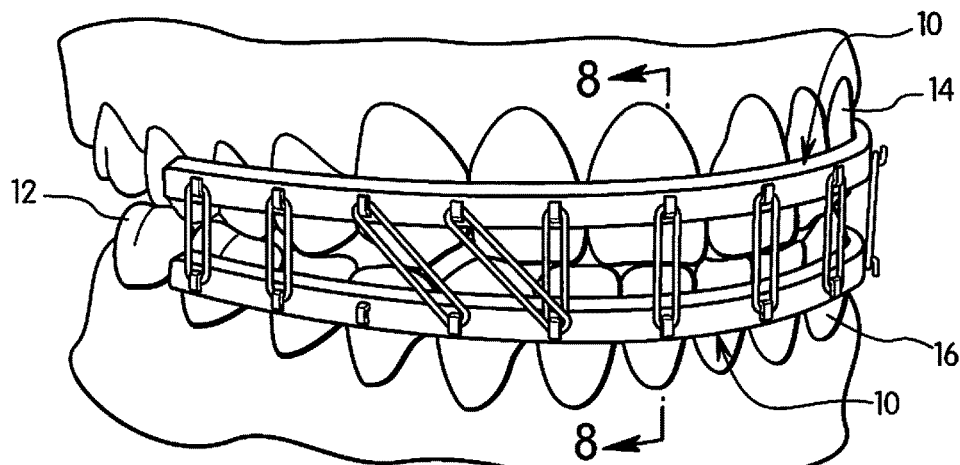
FIG. 1 is a perspective view of a pair of dental arch bars that are directly bonded to a patient's upper and lower teeth without using circumdental wiring in accordance with one illustrative embodiment.
Figure 2:
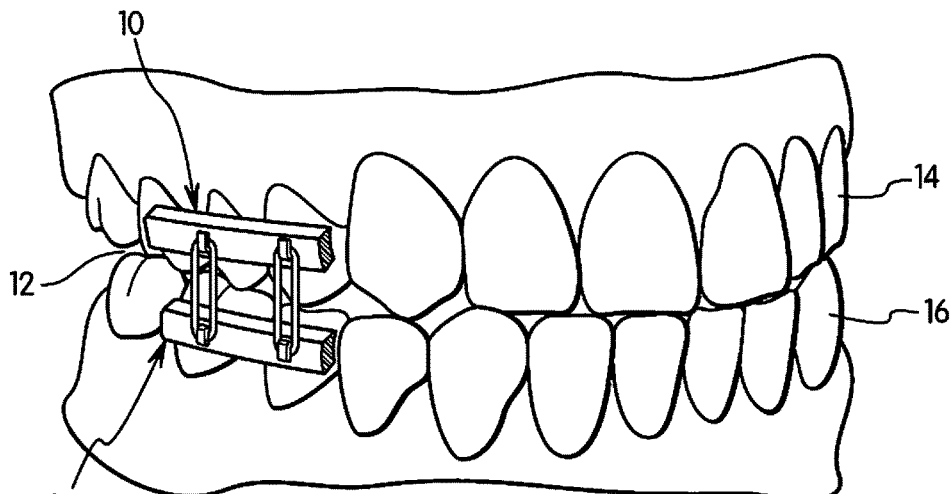
FIG. 2 is a perspective view, similar to FIG. 1, of a pair of dental arch bars that are directly bonded to a patient's upper and lower teeth without using circumdental wiring but wherein the arch bars have been cut to a desired length.
Figure 3:
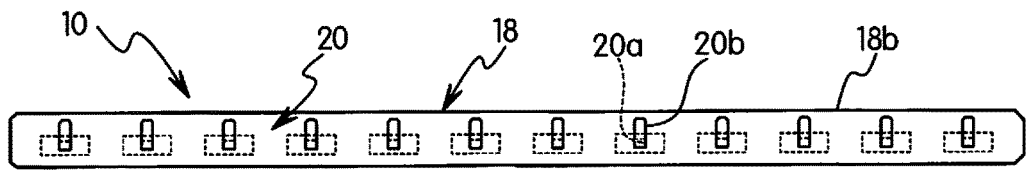
FIG. 3 is a facial side elevational view of the upper arch bar illustrated in FIG. 1 in its prior to use condition with attachment members embedded in the pliable splint.
Figure 4:
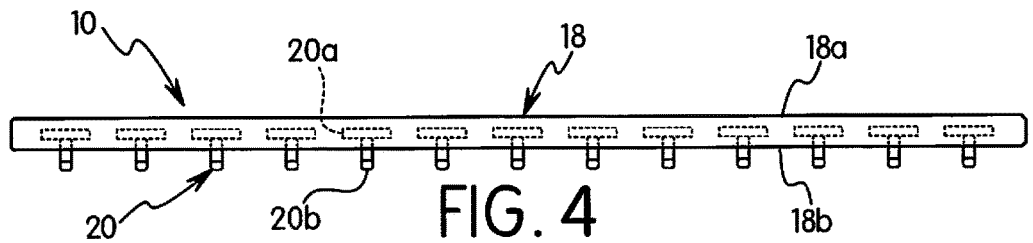
FIG. 4 is a top plan view of the upper arch bar illustrated in FIGS. 1 and 3 showing the gingival edge of the upper arch bar in its prior-to-use condition with attachment members embedded in the pliable splint.
Figure 5:
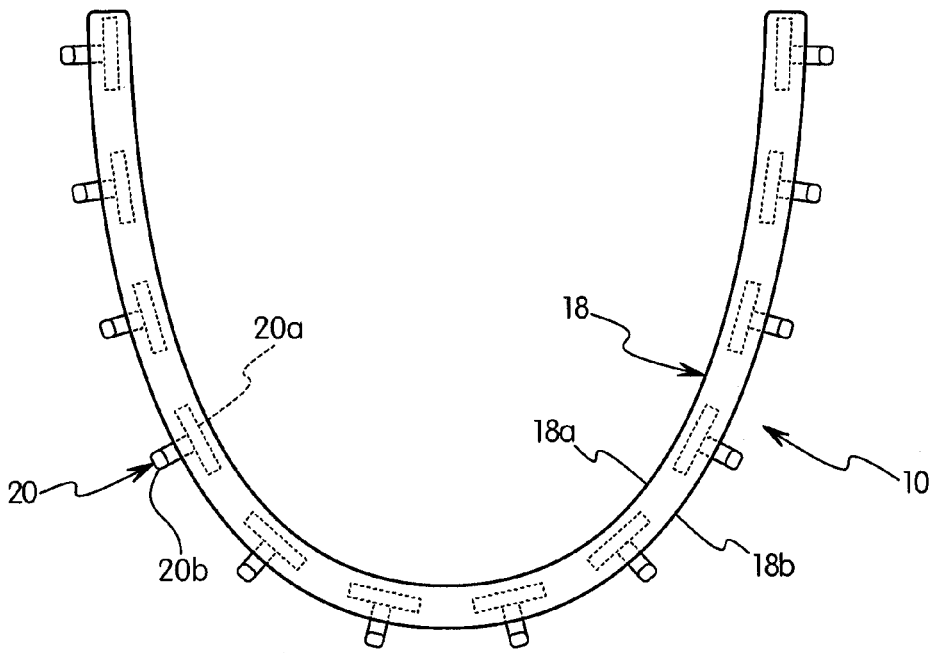
FIG. 5 is a top plan view of the upper arch bar illustrated in FIGS. 1, 3 and 4 showing the gingival edge of the upper arch bar after being deformed to a use condition with attachment members embedded in the pliable splint.
Figure 6:
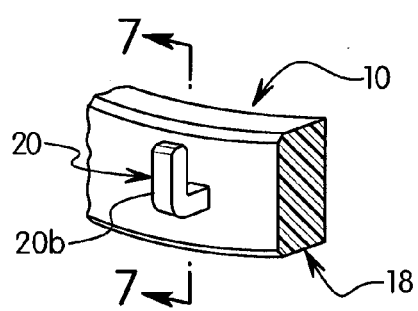
FIG. 6 is a partial perspective view of a portion of the upper arch bar illustrated in FIG. 5.

Referring initially to FIGS. 1 and 2, a resin MMF/reimplantation device (e.g., an intermaxillary fixation arrangement) is illustrated that includes upper and lower dental arch bars 10 and a plurality of elastomeric ligature connectors 12 in accordance with one illustrative embodiment. As seen in FIGS. 1 and 2, the upper and lower dental arch bars 10 are directly bonded to a patient's upper and lower teeth 14 and 16, respectively, without using circumdental wiring in accordance with one illustrative embodiment.

As illustrated in FIGS. 1 and 2, the patient's jaw is held closed by the elastomeric ligature connectors 12 interconnecting the upper and lower dental arch bars 10. While elastomeric ligature connectors (e.g., rubber bands) are illustrated for interconnecting the upper and lower dental arch bars 10, it will be apparent to those skilled in the dental field from this disclosure that other types of ligature connectors can be used such as metal inter-arch wire loops (e.g., twenty-six gauge wire). Moreover, the elastomeric ligature connectors 12 are not limited to the depicted arrangements of FIGS. 1 and 2. Rather, the arrangement of the elastomeric ligature connectors 12 will depend upon the particular patient's condition.

In FIG. 2, the dental arch bars 10 have been cut to a shorter length to illustrate the versatility of the dental arch bars 10. While the dental arch bars 10 have been cut to the same length, it will be apparent to those skilled in the dental field from this disclosure that the dental arch bars 10 can be cut to different lengths as needed and/or desired. The dental arch bars 10 will hereinafter be primarily discussed with respect to its uncured or pre-cured state, unless otherwise specified.

As illustrated in FIG. 1, the upper and lower dental arch bars 10 are identical. However, the upper and lower dental arch bars 10 have opposite orientations (i.e., generally mirror images of each other) when bonded to a patient's upper and lower teeth 14 and 16. Thus, each of the upper and lower dental arch bars 10 will be hereinafter merely referred to as the dental arch bar 10. Of course, the upper and lower dental arch bars 10 do not need to be identical. In FIGS. 1 to 3, the upper and lower dental arch bars 10 have been cured (i.e., hardened) and adhesively bonded to the patient's upper and lower teeth 14 and 16.

Referring now to FIGS. 4 to 8, the dental arch bar 10 will be discussed in more detail in its uncured state. Basically, the dental arch bar 10 includes an elongated pliable splint 18 and a plurality of individual spaced apart attachment members 20. In FIGS. 4 to 8, the attachment members 20 are pre-embedded in the pliable splint 18 prior to placing the pliable splint 18 on the patient's teeth. By having the attachment members 20 pre-embedded in the pliable splint 18, the dental arch bar 10 can be quickly installed without the need of an additional step of inserting the attachment members into the pliable splint 18. Once the pliable splint 18 is in place on the patient's teeth, the pre-embedded attachment members 20 can be adjusted if necessary. However, alternatively, the attachment members 20 can be embedded in the pliable splint 18 after the pliable splint 18 is placed on the patient's teeth as explained below.

In the embodiment of FIGS. 4 to 8, the pliable splint 18 constitutes a pliable base member of the dental arch bar 10 that is a one-piece, unitary member. The pliable splint 18 is formed of a moldable material that deforms under pressure to a contour of a patient's teeth. One example of a light-curing composite resin that can be used for the pliable splint 18 is Revotek LC™, which is sold by GC America Inc. Preferably, the moldable material of the pliable splint 18 is deformable and moldable in all directions. The term "pliable" as used herein means a material that has a plasticity such that the material retains a shape attained by pressure deformation (i.e., molded or altered). Here, the pliable splint 18 has a plasticity such that the material retains a shape attained by pressure deformation in all directions.

Now, the first embodiment of FIGS. 1 to 8 will be discussed in more detail. Each of the attachment members 20 includes an anchoring portion 20a and a protuberance portion 20b. The anchoring portion 20a is at least partially embedded in the pliable splint 18. The anchoring portion 20a preferably has a non-circular cross section that resists turning and/or other movement of the attachment member 20 relative to the pliable splint 18. However, the attachment members 20 are adjustable relative to the pliable splint 18 by applying pressure to the attachment members 20 due to the pliable nature of the pliable splint 18. In other words, the anchoring portions 20a of the attachment members 20 are adjustably supported in the pliable splint 18 without deforming the attachment members 20. The protuberance portion 20b extends from the anchoring portion 20a and out of the pliable splint 18 to form an attachment point for the elastomeric ligature connectors 12. The protuberance portion 20b of the attachment members 20 are illustrated as hooks. In the illustrated embodiment, the protuberance portions 20b (e.g., the hooks) of the attachment members 20 are equally spaced apart by about eight millimeters. However, it will be apparent to those skilled in the dental field from this disclosure that other shapes, such as studs, can be used for the protuberance portion 20b of the attachment members 20, and that any suitable spacing between the protuberance portions 20b the attachment members 20 can be used as needed and/or desired. The attachment members 20 are hard rigid members that can be made of any suitable material such as stainless steel.

As explained below, the pliable splint 18 is cured to form a hard rigid splint that can stabilize the patient's teeth and/or jaw. However, in the uncured or pre-cured state, the pliable splint 18 is preferably formed of a moldable material that retains its shape upon bending. In particular, the pliable splint 18 is constructed of a material that is moldable to conform to the shape of the patient's teeth, and that is subsequently curable to a rigid member that is sufficient to stabilize the patient's teeth and/or jaw. Preferably, the material of the pliable splint 18 has a viscosity of modeling clay such that the dental arch bars 10 do not sag at room temperature (e.g., in a range of about sixty-two degrees Fahrenheit to about eighty-five degrees Fahrenheit). In the illustrated embodiment, the material of the pliable splint 18 is a light curable resin composite having a light curable component. Of course, the material of the pliable splint 18 can have other components for strength as needed and/or desired. Also the composite resin of the pliable splint 18 have a dual-cure property (light-curable and self-curable) if needed and/or desired. In any case, the pliable splint 18 is formed of a non-flowable material with a self-supporting (non-sagging) viscosity and a moldable property. The pliable splint 18 is basically a putty stick that won't appreciably (i.e., noticeably with the human eye) droop or sag when held at one end in a cantilever manner over a period of time of at least one minute, but is bendable and moldable under pressure. Thus, the pliable splint 18 is a malleable resin with a plasticity such that the pliable splint 18 retains a shape attained by pressure deformation (i.e., molded or altered). Various self-supporting light-curable composites are known that can be used for the pliable splint 18. However, the material of the pliable splint 18 is not limited to a light curable material. The pliable splint 18 can be cured (i.e., hardened) in other ways such as using heat to cure the material of the pliable splint 18, or using an autopolymerizing polymethylmethacrylate material for the pliable splint 18.

Figure 7:
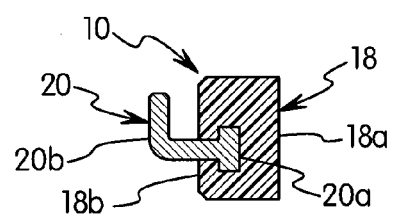
FIG. 7 is a cross sectional view of the upper arch bar as seen along section line 7-7 of FIG. 6 showing one of the attachment members embedded in the pliable splint.
Figure 8:
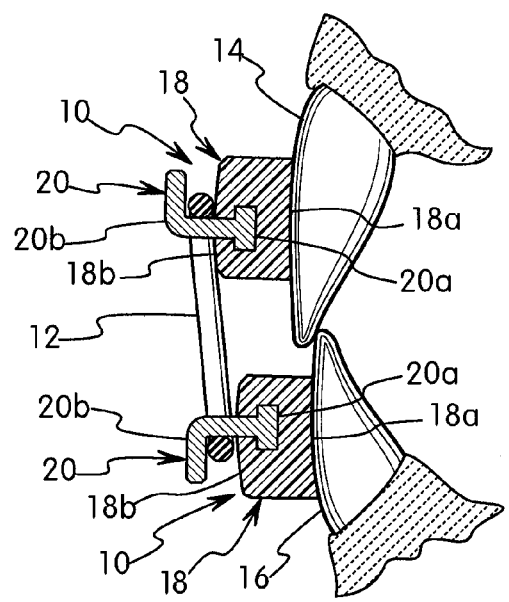
FIG. 8 is a cross sectional view of the upper and lower arch bars directly bonded to a patient's upper and lower teeth as seen along section line 8-8 of FIG. 1.
Figure 9:
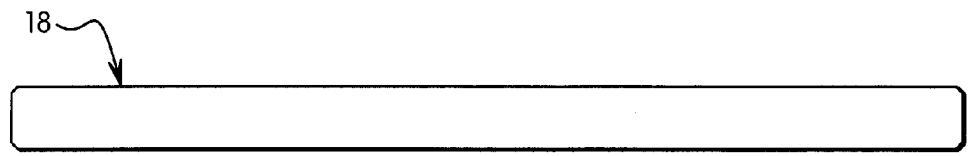
FIG. 9 is a facial side elevational view of the pliable splint for either the upper arch bar or the lower arch bar illustrated in FIG. 1 in its prior to use condition and prior to embedding the attachment members in the pliable splint.
Figure 10:
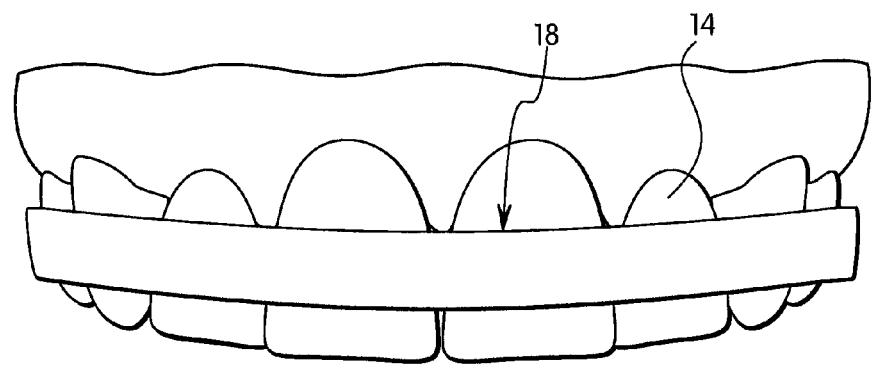
FIG. 10 is an elevational view of a pliable splint without the attachment members being directly bonded to a patient's upper teeth and without using circumdental wiring.
Figure 11:
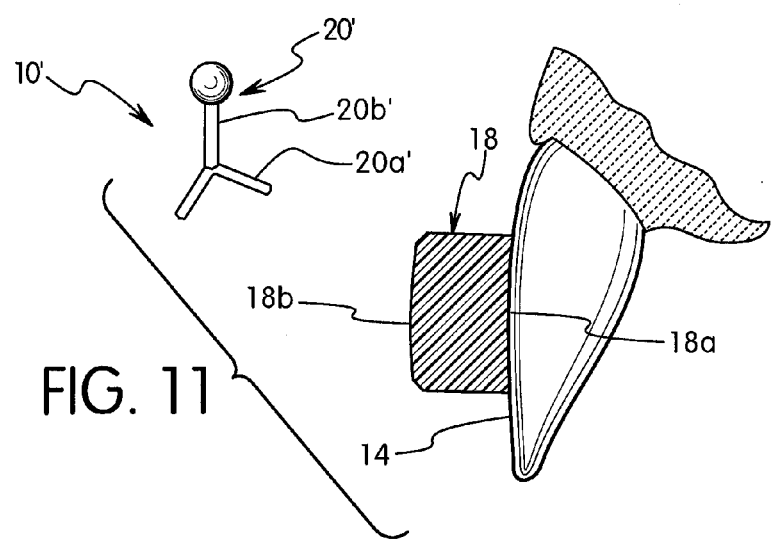
FIG. 11 is an exploded cross sectional view of the pliable splint directly bonded to a patient's upper teeth as seen along section line 11-11 of FIG. 10 with one of the attachment members being located to be embedded into the pliable splint.
Figure 12:
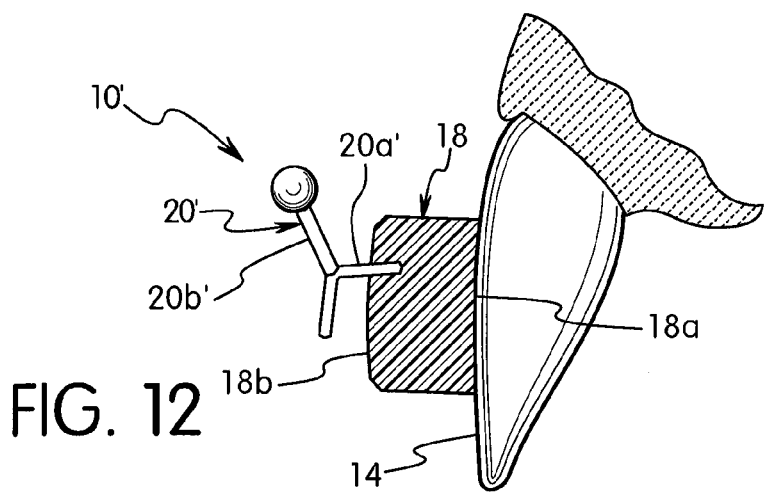
FIG. 12 is a cross sectional view of the pliable splint directly bonded to a patient's upper teeth with one of the attachment members being partially embedded into the pliable splint.
Figure 13:
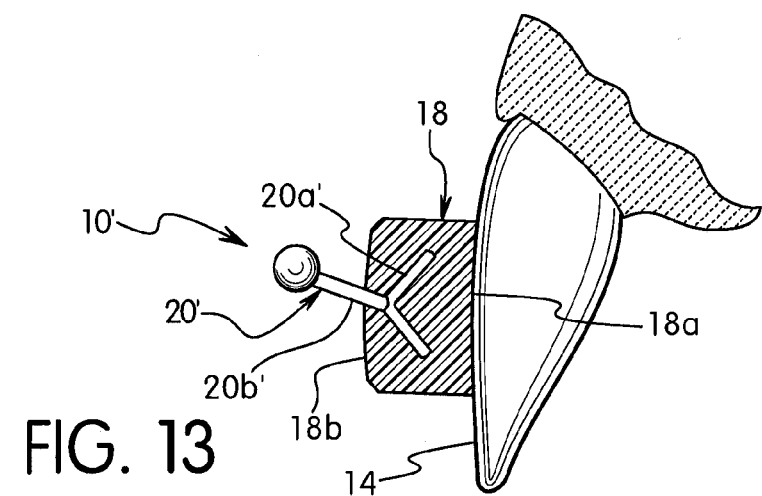
FIG. 13 is a cross sectional view of the pliable splint directly bonded to a patient's upper teeth with one of the attachment members being fully embedded into the pliable splint.
Figure 14:
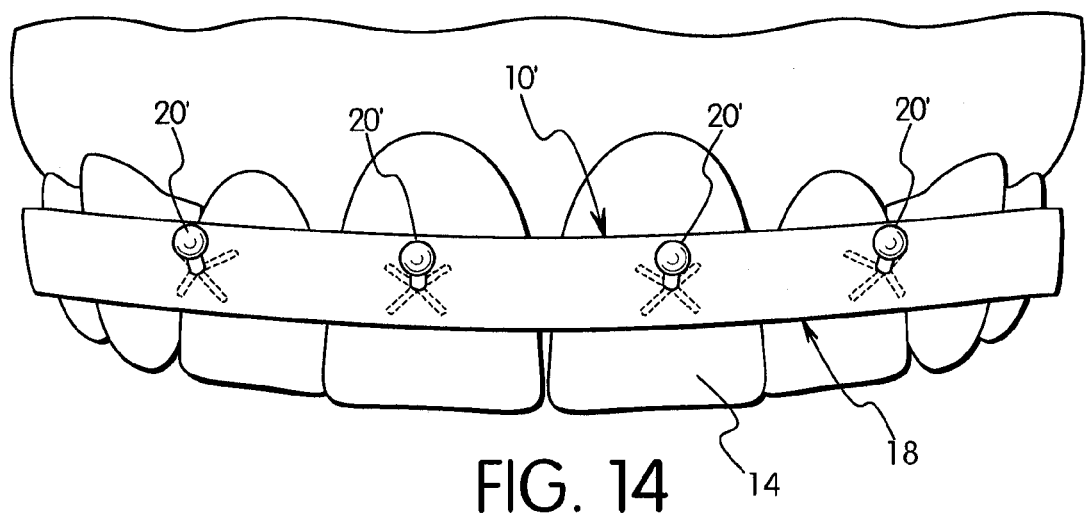
FIG. 14 is an elevational view of the pliable splint being directly bonded to a patient's upper teeth without using circumdental wiring and the attachment members being fully embedded into the pliable splint after the pliable splint directly bonded to the patient's upper teeth.

The pliable splint 18 includes an interiorly facing side surface 18a and an exteriorly facing side surface 18b. The interiorly facing side surface 18a contacts the surface of the patient's teeth and conforms to the shape of the patient's teeth. While the protuberance portion 20b of the attachment members 20 are illustrated as extending out of the exteriorly facing side surface 18b, the attachment members 20 can be configured such a protuberance portion extends out of top and/or bottom of the pliable splint 18 as needed and/or desired. Moreover, while the surfaces 18a and 18b are illustrated as generally flat, parallel surfaces in its original unused state as seen in FIG. 7, the pliable splint 18 can have a variety of transverse cross sections as explained below.

The pliable splint 18 has a viscosity such that the attachment members 20 normally remain stationary in the pliable splint 18. However, preferably, the relative position and/or orientation of the attachment members 20 relative to the pliable splint 18 can be physically adjusted within a prescribed amount without compromising the overall integrity of the dental arch bar 10 when cured. The light-curable resin component of the pliable splint 18 cures to a rigid state in less than one minute upon application of a curing source. More preferably, the light-curable resin component of the pliable splint 18 cures to a rigid state in in about twenty to thirty seconds upon application of a curing source having a prescribed wavelength (e.g., 840 nanometers). Preferably, the curing wavelength of the light-curable resin component of the pliable splint 18 is within the visible light spectrum. The light-curable resin component of the pliable splint 18 will cure under regular ambient light, but will cure faster when subjected with higher powered and more focused spectrum light.

Now, referring to FIGS. 9 to 14, a dental arch bar 10' in accordance with a second embodiment will be discussed. Here, the dental arch bar 10' includes the pliable splint 18 of the first embodiment, as discussed above, and a plurality of attachment members 20'. The attachment members 20' are designed to be embedded in the pliable splint 18 after the dental arch bar 10 is placed on the patient's teeth. By waiting to embed the attachment members 20' into the pliable splint 18 until after the dental arch bar 10 is placed on the patient's teeth, the attachment members 20' can be precisely placed as needed and/or desired for the particular patient. Each of the attachment members 20' includes an anchoring portion 20a' and a protuberance portion 20b'. In this embodiment, the protuberance portion 20b' is a rod with a spherical free end, while the anchoring portion 20a' is formed by four diverging spikes or rods. Of course, the attachment members 20' are not limited to the illustrated shapes.

Now, one potential procedure will now be discussed for using the dental arch bars 10 or 10' of the present disclosure, which are to be directly bonded onto the tooth enamel of the upper and lower teeth 14 and 16 as illustrated in FIGS. 1 and 2. Of course, the use of the dental arch bars 10 or 10' of the present disclosure is not limited to the following procedure. In other words, the order of some of the steps can be changed as needed and/or desired.

First, the dental arch bars 10 or 10' are cut to the appropriate lengths for the intended procedure such as, for example, the two procedures illustrated in FIGS. 1 and 2. Next, the procedure of directly bonding the dental arch bars 10 to the rows of the upper and lower teeth 14 and 16 may be carried out by first removing plaque and/or other substances from the exterior tooth surface of the upper and lower teeth 14 and 16 by any conventional procedure such as using a standard toothbrush with conventional toothpaste. Alternatively, the upper and lower teeth 14 and 16 may be cleansed further with chlorohexadine gluconate for further removing any substances remaining on the surfaces of the upper and lower teeth 14 and 16.

After the plaque and/or other substances has been removed from the upper and lower teeth 14 and 16, then an acid etching gel may be used on the outer surfaces of the upper and lower teeth 14 and 16 for micro-mechanical retention. The acid etching gel may be of a material such as phosphoric acid etchant or other suitable etchant. The teeth can be etched with a thirty-two to thirty-seven percent phosphoric acid solution or gel for fifteen to twenty seconds. The acid etching gel is then rinsed off with water or saline. A frosted appearance will show when the teeth have been dried. In the case a patient having a crown and/or a bridge, a two percent hydroflouric gel can alternatively be used to etch the crown and/or the bridge.

Following the application of etching gel and after the upper and lower teeth 14 and 16 have been substantially dried, a dental bonding agent is applied and light cured for a few seconds. Dental bonding agents come in one and two step version. Alternatively, an all in one etching-bonding agent can be used to combine the above mentioned steps. After the upper and lower teeth 14 and 16 have been properly primed with the dental bonding agent, the dental bonding agent is then light cured for a few seconds. Alternatively, a one-step product can be used that performs etching, priming and bonding in a single application.

Now, applied after the bonding agent is cured, the dental arch bars 10 or 10' are manually placed against the upper and lower teeth 14 and 16, such that the pliable splints 18 extend the desired amount for the intended procedure, e.g., from the first molar on one side of patient to the first molar on a second side of the patient. If the dental arch bars 10 have the pre-embedded attachment members 20, then the pre-embedded attachment members 20 can be adjusted as necessary. In the case of the dental arch bars 10', the attachment members 20' can be precisely placed in the pliable splints 18 after one or both of the dental arch bars 10' are attached to the patient's teeth. In this way, the dental arch bars 10' are customized as needed and/or desired to meet the needs of the particular patient. In either case, the pliable splints 18 will typically need to be cured for ten to twenty seconds per area depending on the intensity of the curing source. While the curing of the pliable splints 18 are performed after both of the elongated pliable splints 18 are placed on the upper and lower teeth of the patient, the order of the procedure can be changed as needed and/or desired. For example, a first one of the pliable splints 18 can be placed on one of the upper and lower teeth of the patient and then cured before a second one of the pliable splint 18 is placed on the other of the upper and lower teeth of the patient and then subsequently cured.

Once the both of the pliable splints 18 have been cured, the upper and lower jaws are drawn together by applying the elastomeric ligature connectors 12. The elastomeric ligature connectors 12 are looped around adjacent ones of the attachment members 20 that project from the pliable splints 18. Of course, other types of connectors can be used as needed and/or desired.

After an appropriate term of healing and recovery, the elastomeric ligature connectors 12 are cut, and the pliable splints 18 are debonded from the patient's teeth. Preferably, a debonding plier is used to remove the pliable splints 18.

It will now be appreciated that the dental arch bars 10 of the present disclosure substantially simplifies and improves the direct bonding attachment of a dental splint to a patient's teeth for the restoration and healing of maxillo-mandibular injuries, including the reduction and temporary fixation of teeth, teeth rows and jaw segments.

Figure 15:
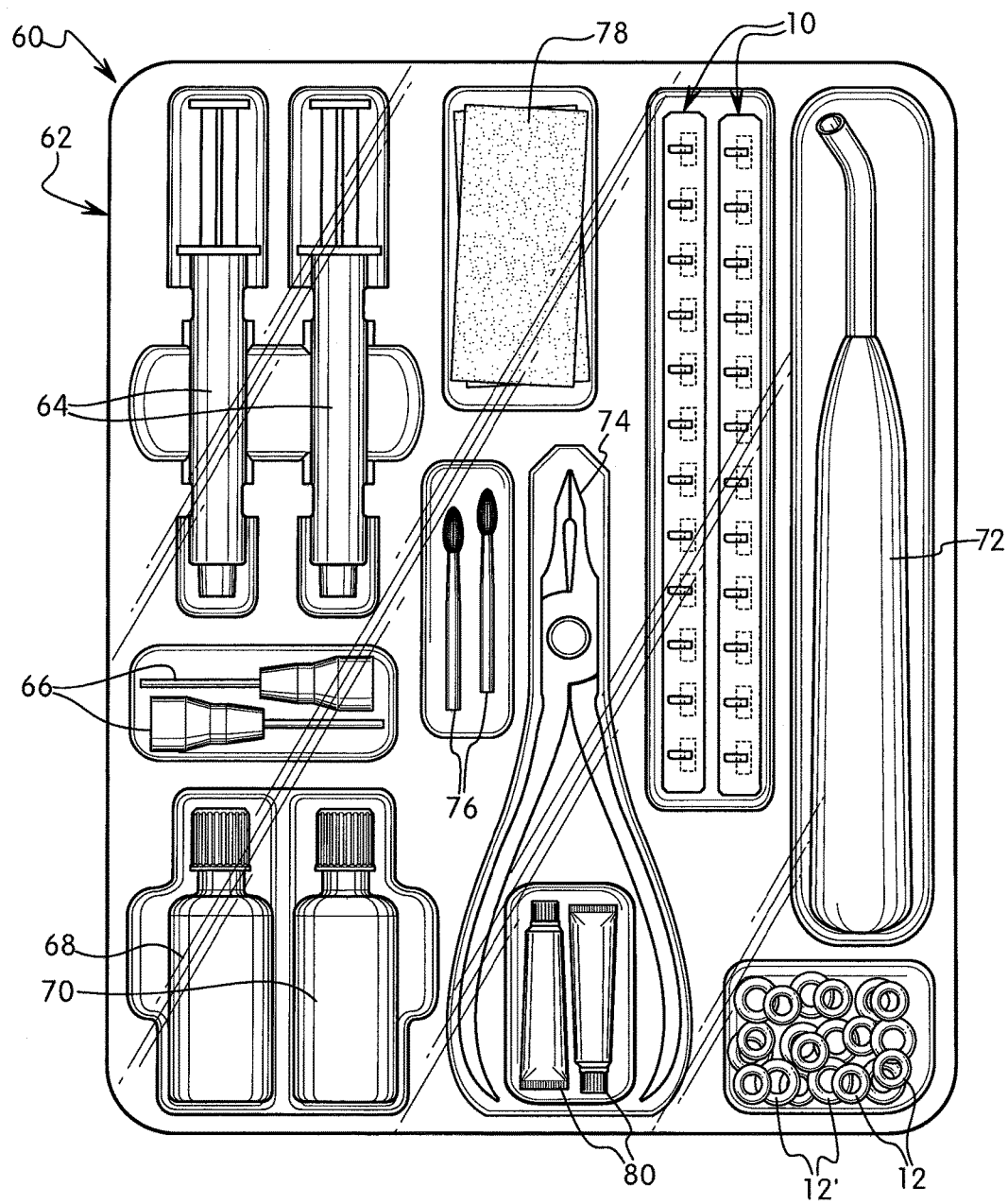
FIG. 15 is a top plan view of a resin MMF/reimplantation kit that includes a pair of the dental arch bar illustrated in FIG. 1 wherein the attachment members are pre-embedded into the pliable splint.
Figure 16:
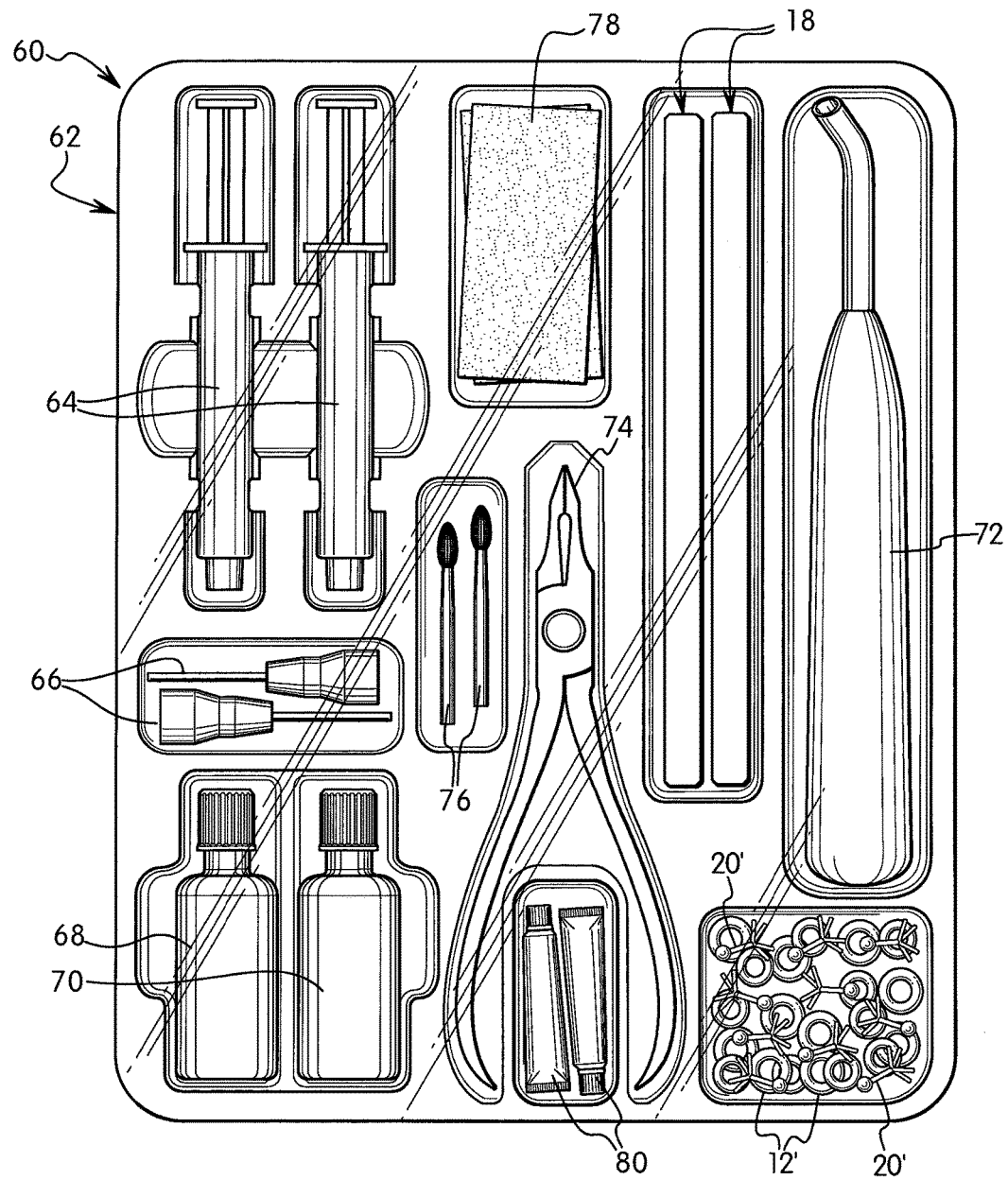
FIG. 16 is a top plan view of an resin MMF/reimplantation kit that includes a pair of the dental arch bar wherein the attachment members are not pre-embedded into the pliable splint.

Referring now to FIGS. 15 and 16, two resin MMF/reimplantation or intermaxillary fixation kits 60 and 60' are illustrated for carrying out the above mentioned procedures of using the dental arch bars 10 or 10' of the present disclosure. Of course, the resin MMF/reimplantation or intermaxillary fixation kits of the present disclosure are not limited to the resin MMF/reimplantation or intermaxillary fixation kits 60 and 60' illustrated in FIGS. 15 and 16. Basically, the resin MMF/reimplantation or intermaxillary fixation kit 60 preferably includes a container 62 that includes a pair of the dental arch bars 10 and a plurality of the elastomeric ligature connectors 12. Preferably, two different sizes of the elastomeric ligature connectors 12 are provided in the intermaxillary fixation kit 60. For example, the elastomeric ligature connectors 12 can be ⅜ inch or ¼ inch non-latex elastics with some of the elastics having a medium force of four ounces and some of the elastics having a heavier force of six ounces. Instead of the elastomeric ligature connectors 12, the intermaxillary fixation kit 60 could be provided with ligature wires.

The intermaxillary fixation kit 60 preferably further includes two acid etching gel syringes 64 of thirty-two to thirty-seven percent phosphoric acid solution or gel, two applicator tips 66 and 68, a primer 68, a dental bonding agent 70, a light curing device 72, a removal or debonding tool 74 (e.g., a debonding plier), a pair of rotary instrument 76, two pieces of fine sandpaper 78 and two additional etchant gel tubes 80 for crowns and bridges. All of these items of the intermaxillary fixation kit 60 are conventional items, except for the dental arch bars 10. The light curing device 72 is configured to output a light having a prescribed wavelength that cures the curable component of the pliable splints 18 upon application of the light on the pliable splints 18 for a prescribed period of time. The light curing device 72 will depend on the type of material selected for the pliable splints 18. The rotary instrument 76, and the sandpaper 78 are provided to roughen ceramic surfaces such as crowns and bridges so that the dental arch bars 10 can be bonded to them as well, if necessary. Optionally, the debonding tool 74 is included for removing the dental arch bars 10.

The resin MMF/reimplantation or intermaxillary fixation kit 60' is identical to the resin MMF/reimplantation or intermaxillary fixation kit 60, except that instead of the dental arch bars 10, the resin MMF/reimplantation or intermaxillary fixation kit 60' has two of the pliable splints 18 without pre-embedded attachment members and a plurality of individual attachment members 20'.

Figure 17:
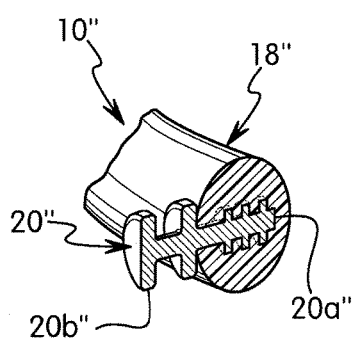
FIG. 17 is a cross sectional view, similar to FIG. 7, of an upper arch bar having an alternative configuration of the pliable splint.

Referring now to FIG. 17 illustrates an alternative dental arch bar 10" that has a pliable splint 18" with a circular transverse cross section. It will be apparent to those skilled in the dental field that the shape of the pliable splint is not limited to a rectangular or circular transverse cross section as illustrated. The pliable splint 18" is identical to the pliable splint 18, except for its transverse cross sectional shape. The dental arch bar 10' of FIG. 17 can have a plurality of pre-embedded attachment members 20" (only one shown), or attachment members can be embedded into the pliable splint 18" after attaching the pliable splint 18" to the patient's teeth. The attachment members 20" are longitudinally spaced similar to the first embodiment if pre-embedded. Here, each of the attachment members 20" includes an anchoring portion 20a" and a protuberance portion 20b". The shapes of the anchoring portions 20a" and the protuberance portions 20b" are not limited to the illustrated shapes. For example, in the case of an attachment member that is shaped as a stud, the anchoring portion can be a post shape with or without annular ribs. Also, the attachment members are not limited to one-piece members as illustrated. For example, the protuberance portion can be attached to the anchoring portion in a removable manner such as using a screw type connection.

Figure 18:
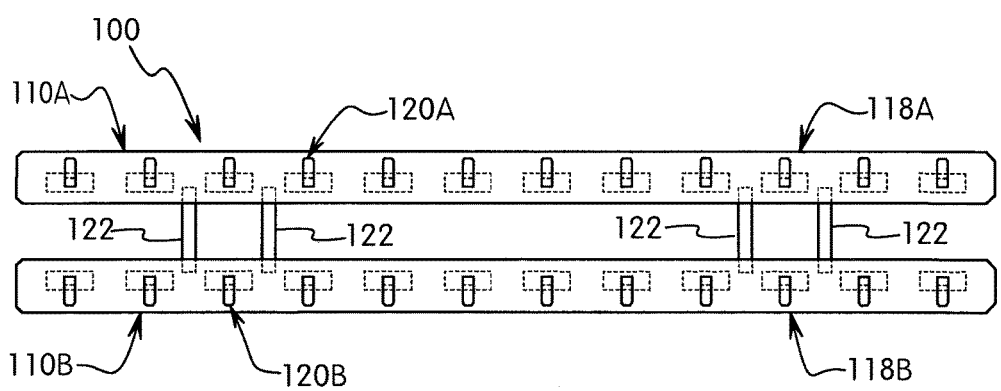
FIG. 18 is a facial side elevational view of an integrated upper-lower arch bar illustrated in FIG. 1 accordance with another illustrative embodiment.

Referring now to FIG. 18, an integrated upper-lower dental arch bar 100 is illustrated in accordance with another embodiment. Basically, the integrated upper-lower dental arch bar 100 includes an upper dental arch bar 118A, a lower dental arch bar 118B and a plurality of connectors 122. The upper and lower dental arch bars 42 and 44 are connected together by the connectors 122 to form an integrated unit. The upper dental arch bar 110A has an elongated pliable splint 118A and a plurality of attachment members 120A. Similarly, the lower dental arch bar 110B has an elongated pliable splint 118B and a plurality of pre-embedded attachment members 120B. The pliable splints 118A and 118B are identical to the pliable splint 18, discussed above, except that portions of the connectors 122 are embedded into the pliable splints 118A and 118B for interconnecting the pliable splints 118A and 118B together. Of course, it will be apparent from this disclosure that the integrated upper-lower dental arch bar 100 can have attachment members embedded into he pliable splints 118A and 118B after the pliable splints 118A and 118B are attached to the patient's teeth.

In view of the similarity between the integrated upper-lower dental arch bar 100 and the dental arch bar 10, the integrated upper-lower dental arch bar 100 will not be discussed in further detail herein for the sake of brevity. The number of the connectors 122 can be varied as needed and/or desired. Thus, the number of the connectors 122 is not limited to the illustrated embodiment. Preferably, the connectors 122 are flexible connecting members that allow for relative movement of the pliable splints 118A and 118B. The connectors 122 can be formed of a resilient material as needed and/or desired.

The terms of degree such as "substantially", "about" and "approximately" as used herein mean a reasonable amount of deviation of the modified term such that the end result is not significantly changed.

While only selected embodiments have been chosen to illustrate the present invention, it will be apparent to those skilled in the dental field from this disclosure that various changes and modifications can be made herein without departing from the scope of the invention as defined in the appended claims. For example, the size, shape, location or orientation of the various components can be changed as needed and/or desired. Also, although there is no commercially available direct resin system with self-etching capability, common sense says dentists can expect one in the near future. The recent market entries of self-etching resin cements and adhesives systems suggest that the industry is close to developing a restorative system that will have self-etching capability. Thus, a self-etching resin cements and/or adhesives can be used for apply the resin dental arch bars of the present disclosure.

Thus, the foregoing descriptions of the embodiments according to the present invention are provided for illustration only, and not for the purpose of limiting the invention as defined by the appended claims and their equivalents.

What is claimed is:

1. A resin MMF/reimplantation kit comprising:
   a container;
   an elongated pliable splint disposed in the container, the elongated pliable splint including an interiorly facing side surface and an exteriorly facing side surface, the pliable splint including a curable component that cures from a moldable state to a rigid state upon being activated, the elongated pliable splint being in a moldable state while in the container; and
   a plurality of individual attachment members disposed in the container, the individual attachment members including an anchoring portion configured to be at least partially embedded in the pliable splint, and a protuberance portion extending from the anchoring portion to be disposed on the exteriorly facing side surface of the pliable splint upon at least partially embedding the anchoring portion in the elongated pliable splint.

2. The resin MMF/reimplantation kit according to claim 1, further comprising
   a plurality of ligature connectors.

3. The resin MMF/reimplantation kit according to claim 1, further comprising
   an additional elongated pliable splint including a curable component that cures to from a moldable state to a rigid state upon being activated.

4. The resin MMF/reimplantation kit according to claim 1, further comprising
   a light curing device configured to output a light having a prescribed wavelength that cures the curable component upon application of the light on the pliable splint for a prescribed period of time.

5. The resin MMF/reimplantation kit according to claim 2, wherein
   the ligature connectors include two different sizes.

6. The resin MMF/reimplantation kit according to claim 1, further comprising
   a primer and a bonding agent.

7. The resin MMF/reimplantation kit according to claim 1, wherein the curable component of the pliable splint includes a light-curable resin component that is cured in response to application of light having a prescribed wavelength.

8. The resin MMF/reimplantation kit according to claim 7, wherein
the light-curable resin component cures to the rigid state in less than in response to application of light in about twenty to thirty seconds.

9. The resin MMF/reimplantation kit according to claim 1, wherein
the pliable splint is formed of a non-flowable material with a self-supporting viscosity.

10. The resin MMF/reimplantation kit according to claim 1, wherein
the pliable splint is formed of a material having a self-adhesive property with respect to teeth.

11. The resin MMF/reimplantation kit according to claim 1, wherein
the pliable splint is formed of a moldable material that deforms under pressure to a contour of a patient's teeth.

12. An intermaxillary fixation method comprising:
placing a first elongated pliable splint against one of upper and lower teeth of a patient such that the first elongated pliable splint contacts and conforms to the one of the upper and lower teeth;
embedding first individual attachment members in an exteriorly facing side surface of the first elongated pliable splint with the first individual attachment members not protruding from an interiorly facing side surface of the first elongated pliable splint, the interiorly facing side surface of the first elongated pliable splint facing in an opposite direction from the exteriorly facing side surface of the first elongated pliable splint;
curing the first elongated pliable splint from a moldable state to a rigid state while the first elongated pliable splint is disposed against the one of the upper and lower teeth;
placing a second elongated pliable splint against the other of the upper and lower teeth such that the second elongated pliable splint contacts and conforms to the other of the upper and lower teeth;
embedding the second individual attachment members in an exteriorly facing side surface of the second elongated pliable splint with the second individual attachment members not protruding from an interiorly facing side surface of the second elongated pliable splint, the interiorly facing side surface of the second elongated pliable splint facing in an opposite direction from the exteriorly facing side surface of the second elongated pliable splint;
curing the second elongated pliable splint from a moldable state to a rigid state while the second elongated pliable splint is disposed against the other of the upper and lower teeth; and
securing one or more the first and second individual attachment members together with connectors.

13. The intermaxillary fixation method of claim 12, wherein
the curing of the first and second elongated pliable splints are performed after both of the first and second elongated pliable splints are placed on the upper and lower teeth of the patient.

14. The intermaxillary fixation method of claim 13, wherein
the curing of the first elongated pliable splints is performed before the second elongated pliable splint is placed on the other of the upper and lower teeth of the patient.

15. The intermaxillary fixation method of claim 12, wherein
the embedding of the first and second individual attachment members in the exteriorly facing side surfaces of the first and second elongated pliable splints, respectively, is performed before the first and second elongated pliable splints are placed on the upper and lower teeth of the patient.

16. A dental arch bar comprising:
an elongated pliable splint including an interiorly facing side surface and an exteriorly facing side surface, the pliable splint being a moldable, non-flowable material in a moldable state with a self-supporting viscosity that deforms under pressure and retains a shape to conform to a contour of a patient's teeth, the pliable splint including a curable component that cures from the moldable state to a rigid state upon being activated; and
a plurality of individual attachment members spaced apart from one another along a longitudinal direction of the pliable splint, each of the attachment members including an anchoring portion being at least partially embedded in the pliable splint in a state prior to applying the dental arch bar to the patient's teeth, each of the attachment members including a protuberance portion extending outwardly from the exteriorly facing side surface of the pliable splint, the attachment members not protruding from the interiorly facing side surface, which faces in an opposite direction from the exteriorly facing side surface.

17. The dental arch bar according to claim 16, wherein
the curable component of the pliable splint includes a light-curable resin component that is cured in response to application of light having a prescribed wavelength.

18. The dental arch bar according to claim 17, wherein
the light-curable resin component cures to the rigid state in less than in response to application of light in about twenty to thirty seconds.

19. The dental arch bar according to claim 16, wherein
the anchoring portions of the attachment members are adjustably supported in the moldable material of the pliable splint without deforming the attachment members to change orientations of the attachment members with respect to the pliable splint.

20. The dental arch bar according to claim 16, wherein
the anchoring portions of the attachment members extend farther in a longitudinal direction of the pliable splint than in a transverse direction of the pliable splint.

* * * * *